US011389111B2

(12) United States Patent
Bae (10) Patent No.: US 11,389,111 B2
(45) Date of Patent: Jul. 19, 2022

(54) COMMUNICATION DEVICE AND METHODS (71) Applicant: NuVasive Specialized Orthopedics, Inc., San Diego, CA (US)

(72) Inventor: Youngsam Bae, San Diego, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 534 days.

(21) Appl. No.: 16/250,618

(22) Filed: Jan. 17, 2019

(65) Prior Publication Data
US 2019/0150835 A1 May 23, 2019

Related U.S. Application Data (63) Continuation of application No. PCT/US2017/042634, filed on Jul. 18, 2017.
(Continued)

(51) Int. Cl.
*A61B 5/00* (2006.01)
*H02J 50/15* (2016.01)
(Continued)

(52) U.S. Cl.
CPC ............ *A61B 5/4851* (2013.01); *A61B 5/002* (2013.01); *A61B 5/0028* (2013.01); *A61B 5/0031* (2013.01); *A61B 5/686* (2013.01); *A61B 5/746* (2013.01); *A61B 5/7435* (2013.01); *H02J 50/15* (2016.02); *A61B 5/05* (2013.01);
(Continued)

(58) Field of Classification Search
CPC ..... A61B 5/0028; A61B 5/0031; A61B 5/686; A61B 5/4851; A61B 2560/0219
See application file for complete search history.

(56) References Cited

U.S. PATENT DOCUMENTS 5,240,004 A * 8/1993 Walinsky ............... A61B 8/12
29/25.35
8,974,366 B1 3/2015 Radziemski et al.
(Continued)

FOREIGN PATENT DOCUMENTS

CN 101800486 A 8/2010
CN 101856222 A 10/2010
(Continued)

OTHER PUBLICATIONS

Carovac, et al., Application of Ultrasound in Medicine, Sep. 2011, AIM, vol. 19, No. 3, p. 168. (Year: 2011).*
(Continued)

*Primary Examiner* — Daniel L Cerioni
*Assistant Examiner* — Raymond P Dulman
(74) *Attorney, Agent, or Firm* — Hoffman Warnick, LLC (57) ABSTRACT

An implantable device for sensing data includes a subcutaneous sensor configured to couple with an implant. The implantable device is operably configured to wirelessly and transcutaneously transmit data sensed by the subcutaneous sensor. The sensor may be powered wirelessly and transcutaneously. Transmission of data and/or power may be provided by ultrasound sound waves. The sensor may be in electrical communication with a piezoelectric transducer configured to receive the ultrasound sound waves.

20 Claims, 13 Drawing Sheets

Related U.S. Application Data (60) Provisional application No. 62/363,340, filed on Jul. 18, 2016.

(51) Int. Cl.
```
A61B 17/72    (2006.01)
A61B 17/68    (2006.01)
A61B 17/66    (2006.01)
A61B 17/70    (2006.01)
A61B 5/103    (2006.01)
A61B 5/05     (2021.01)
A61B 5/145    (2006.01)
G05G 7/10     (2006.01)
```

(52) U.S. Cl.
CPC ......... *A61B 5/1036* (2013.01); *A61B 5/14539* (2013.01); *A61B 17/66* (2013.01); *A61B 17/7002* (2013.01); *A61B 17/7014* (2013.01); *A61B 17/72* (2013.01); *A61B 17/7216* (2013.01); *A61B 2017/681* (2013.01); *A61B 2560/0219* (2013.01); *A61B 2562/0247* (2013.01); *A61B 2562/0252* (2013.01); *A61B 2562/0271* (2013.01); *A61B 2562/242* (2013.01); *G05G 7/10* (2013.01)

(56) References Cited

U.S. PATENT DOCUMENTS

| | | | |
|---|---|---|---|
| 9,125,627 B2 | 9/2015 | Stein | |
| 10,149,936 B2 | 12/2018 | Forsell | |
| 2004/0193020 A1* | 9/2004 | Chiba | A61B 5/07 600/300 |
| 2006/0009856 A1* | 1/2006 | Sherman | A61B 5/0031 623/20.32 |
| 2007/0049826 A1 | 3/2007 | Willis | |
| 2008/0095714 A1 | 4/2008 | Castella et al. | |
| 2008/0300597 A1* | 12/2008 | Morgan | A61B 17/72 606/62 |
| 2009/0005708 A1 | 1/2009 | Johanson et al. | |
| 2011/0196371 A1 | 8/2011 | Forsell | |
| 2011/0213221 A1 | 9/2011 | Roche | |
| 2012/0179004 A1* | 7/2012 | Roesicke | A61B 5/201 600/301 |
| 2014/0336474 A1 | 11/2014 | Arbabian et al. | |
| 2015/0051466 A1* | 2/2015 | Afroz | A61B 5/053 600/377 |
| 2016/0066803 A1* | 3/2016 | Hu | A61B 5/0031 600/561 |
| 2016/0211924 A1* | 7/2016 | Deng | G08C 23/02 |
| 2018/0145770 A1* | 5/2018 | Oelze | H04B 13/005 |
| 2019/0168004 A1* | 6/2019 | Doguet | H02J 7/00034 |

FOREIGN PATENT DOCUMENTS

| | | |
|---|---|---|
| CN | 204992728 U | 1/2016 |
| JP | 2000-506410 A | 5/2000 |
| JP | 2003-520091 A | 7/2003 |
| JP | 2006-055629 A | 3/2006 |
| JP | 2012-507340 A | 3/2012 |
| JP | 2015-502766 A | 1/2015 |
| WO | 9733513 A1 | 9/1997 |
| WO | WO2012103549 | 8/2012 |

OTHER PUBLICATIONS

Saltzstein. Bluetooth: The Future of Wireless Medical Technology? MDDI Online. Feb. 2002. <URL: https://www.mddionline.com/bluetooth-future-wireless-medical-technology>.

Office Action for Japanese Patent Application No. 2019-502164 dated Mar. 8, 2022.

* cited by examiner

COMMUNICATION DEVICE AND METHODS

CROSS REFERENCE TO OTHER APPLICATIONS

This application claims priority to and the benefit of PCT Application No. PCT/US17/42634 filed Jul. 18, 2017, which claims priority to U.S. Provisional Application No. 62/363,340 filed Jul. 18, 2016, and all contents of both of which are hereby incorporated by reference in their entirety.

FIELD OF THE DISCLOSURE

The present disclosure pertains to the field medical devices. More specifically, the present disclosure pertains to implantable devices comprising a subcutaneous sensor, the devices configured to transmit data transcutaneously.

BACKGROUND

Medical implants have various forces exerted on them in vivo, especially medical implants that are adjustable, such as rotatable or extendable while in a subject or patent. Such adjustable medical implants are used in, for example, limb lengthening and spinal adjustable surgical procedures to treat conditions such as limb deformities and scoliosis, respectively. Typically, these adjustable medical implants are secured to one or more bones and gradually adjusted over time until the desired outcome is achieved.

However, these surgical implants and procedures do not include an accurate and non-invasive means of in vivo measurement of conditions, such as force, present at the implant site, particularly after the implant is implanted and during the course of treatment (i.e., adjustments of the adjustable implant). What is needed is some kind of device and method to perform the needed measurement of conditions present at the implant site non-invasively and in vivo.

BRIEF DESCRIPTION OF THE DRAWINGS

To further illustrate the advantages and features of the present disclosure, a more particular description of the invention will be rendered by reference to specific embodiments thereof which are illustrated in the appended drawings. It is appreciated that these drawings are not to be considered limiting in scope. The invention will be described and explained with additional specificity and detail through the use of the accompanying drawings in which.

SUMMARY OF THE DISCLOSURE

In a first aspect, the present disclosure provides a system including an implantable device for sensing data. The implantable device includes a subcutaneous sensor configured to couple with an implant. The implant may be a spinal rod, an intramedullary rod, or a spinous process spacer. The device is operably configured to wirelessly and transcutaneously transmit data sensed by the subcutaneous sensor. The device may be configured to operably receive energy from ultrasound sound waves and provide energy to the subcutaneous sensor. The ultrasound sound waves may have a frequency of greater than about 20 kilohertz. The device may include a piezoelectric transducer in communication with the subcutaneous sensor. The piezoelectric transducer may be configured to transcutaneously receive energy by ultrasound sound waves. The piezoelectric transducer may be configured to wirelessly and transcutaneously transmit the sensed data. The wirelessly transmitted sensed data may be transmitted by short-wavelength ultra high frequency radio waves in the medical radio band from about 2.4 to 2.485 GHz. The wirelessly transmitted sensed data may be transmitted by ultrasound sound waves.

In a second aspect, the present disclosure provides a method of transcutaneously transmitting data from a subcutaneous sensor positioned within a subject. The method includes transcutaneously transmitting wireless power to the subcutaneous sensor, sensing data with the subcutaneous sensor, and transcutaneously transmitting sensed data from the subcutaneous sensor. The sensed data may be force data, temperature data, electrical data, pH data, distance data, pressure data, biomolecular data, or a combination thereof. The sensed data may be received by a receiver subcutaneous or external to skin. The receiver may be configured to transcutaneously transmit data to a mobile device. The sensed data may be transmitted to the mobile device by short-wavelength ultra high frequency radio waves in the medical radio band from about 2.4 to 2.485 GHz. The method may include amplitude modulating the sensed data during the wireless transmission.

In a third aspect, the present disclosure provides an implant kit. The implant kit includes an implant configured to be implanted in a subject, and a subcutaneous force sensor configured to couple with the implant. The subcutaneous sensor is configured to wirelessly receive power.

DETAILED DESCRIPTION

Although particular embodiments of the present disclosure have been described, it is not intended that such references be construed as limitations upon the scope of this disclosure except as set forth in the claims.

Figure 1:
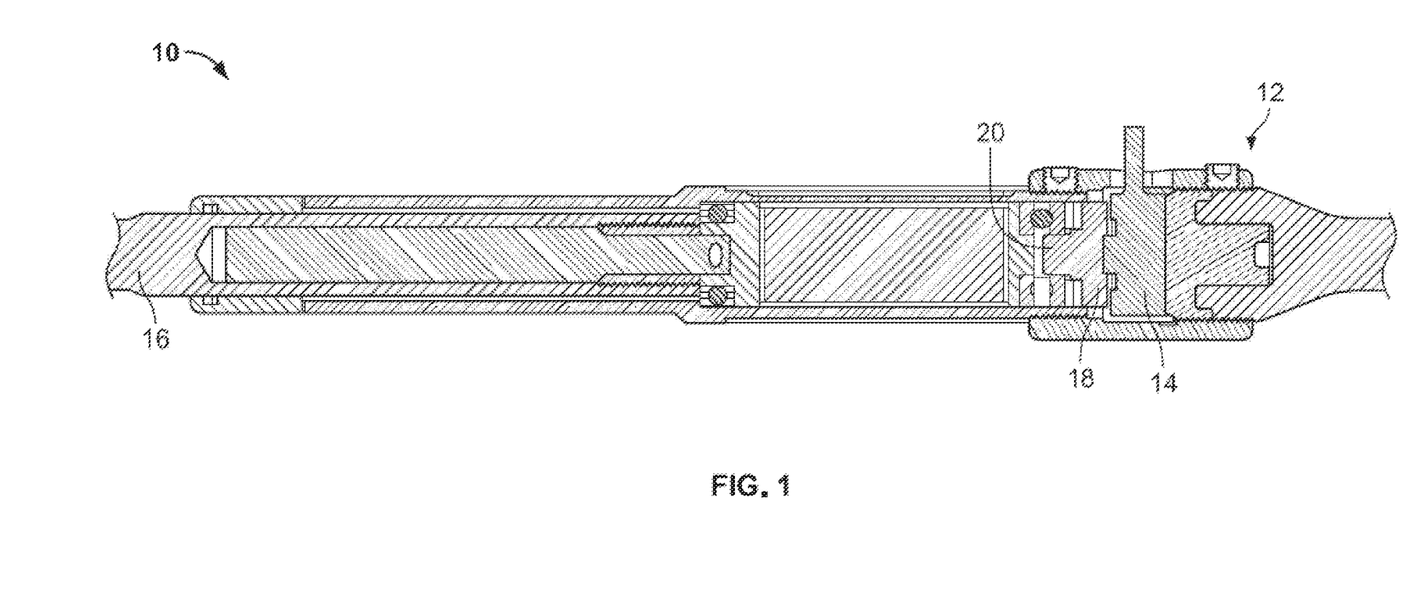
FIG. 1 shows a cross-sectional view of an embodiment of a sensor system.
Figure 2:
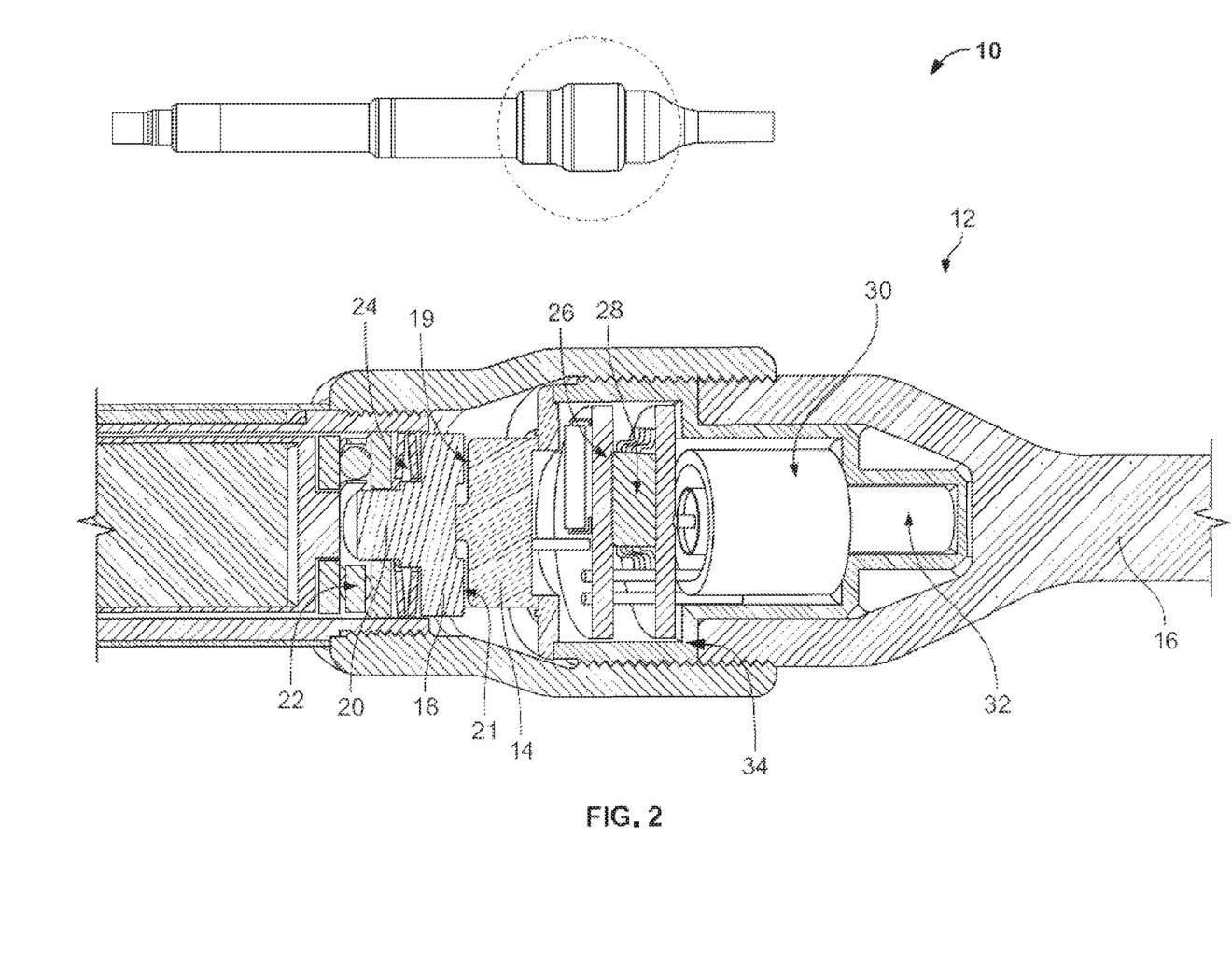
FIG. 2 shows a detailed cross-sectional view of another embodiment a sensor system.

Referring to FIGS. 1 and 2, an embodiment of the system 10 includes an implantable device 12 for implantation in a subject or patient 2, particularly a human. The human subject 2 may be of any age or size. Implantable device 12 includes one or more subcutaneous sensors 14 configured to be coupled, or coupled, to an implant 16. The sensor 14 may measure force, temperature, electricity, pH, distance, pressure, and biomolecules, and may transmit data including these measurements. In embodiments of the system 10 where the sensor 14 is a force sensor, the sensor 14 may measure force between 0 and 300 pounds, 0 and 200 pounds, 0 and 100 pounds, 0 and 50 pounds, or any subrange thereof. The sensor 14 may be, for example, capacitive, resistive, strain gauge, micro-mechanical, piezoelectric, or any combination thereof. Sensed data also may have a data accuracy. In the case of force, the sensor 14 may have a data accuracy of +/−5 pounds, +/−2 pounds, +/−1 pound, +/−0.5 pound, or any subrange thereof.

The implant 16 may be, by way of example, a spinal rod or an intramedullary rod. The sensor 14 may contact a force-load coupler 18 configured to interface between the implant 16 and the sensor 14. The force-load coupler 18 may have a surface 19 that is shaped complementary to a contacted surface 21 of the sensor 14 where the coupler 18 and the sensor 14 interface such that the sensor 14 and the coupler 18 resist lateral movement. The coupler 18 may have a cam 20 integrally formed in the coupler 18 and positioned on the side of coupler 18 that is opposite from sensor 14. One or more thrust bearings 22 may be formed within the implant 14 and disposed on opposite sides of the cam 20 to transfer force from the implant 14 to the coupler 18 and thus to the sensor 14. One or more anti-backout washers 24 may be positioned between the thrust bearing 22 and the coupler 18 such that the device 12 will resist loosening when the device 12 is subjected to vibration.

The sensor 14 may be in communication with a circuit board 26, such as a printed circuit board, and the sensor 14 may transmit sensed data to the circuit board 26. The circuit board 26 is configured to receive the sensed data from the sensor 14 and to communicate the data to a controller 28 (e.g., a microcontroller) for processing and/or temporary or permanent storage on a memory (not shown). The controller 28 may be configured to transmit data to a transmitter 30. The controller 28 may be configured to lower, or eliminate power consumption, when the system 10 is not being used.

The transmitter 30 may be, for example, a tubular piezoelectric transducer. The transmitter 30 may be secured within the implant 16 with, for example, epoxy. In embodiments of the system 10 employing a tubular piezoelectric transducer, the tubular geometry allows the piezoelectric transducer to fit in tubular implants 16, such as spinal rods and intramedullary nails. And, owing to radial mode of the vibration, the tubular transducer propagates data radially, covering 360 degrees. Polyimide film with silicone adhesive (for example, KAPTON® tapes) may be disposed between the transmitter 30 and the implant 16 to isolate the transmitter from the implant 16.

The circuit board 26 may include a frequency synthesizer (i.e., creates carrier waves for piezoelectric transducer 30), power amplifier and noise filters (i.e., conditions carrier wave), power and read strain gauge (i.e., force sensor controls), and may be configured to adjust carrier waves, power, etc. (such as by computer executable instructions that interface with a user via a graphical user interface, as discussed below).

The transmitter 30 may be configured to send and receive wireless signals, such as ultrasound sound waves carrying data, and receive power, such as from ultrasound sound waves. These ultrasound sound waves may be in any frequency of ultrasound, but are generally greater than about 20 kilohertz. In an embodiment, the frequency of ultrasound sound waves is between 200 and 400 kilohertz or is about 300 kilohertz. Benefits of utilizing ultrasound sound waves for power and/or data transmission include that ultrasound sound waves: (1) propagate through metal or solid mediums (e.g., metallic medical implants), and (2) send data transcutaneously through various human skin.

The transmitter 30 may be configured to transmit data and/or power transcutaneously (i.e., from within the subject 2 and across the skin of the subject 2 such that the data and/or power may be received externally from the subject 2. Additionally, power may be received by the transmitter 30 from external from the subject 2. A battery, or capacitor, 32 may be in electric communication with the transmitter 30 such that the battery 32 can store power received from the transmitter 30 and transmit stored power to the transmitter 30, the controller 28, the circuit board 26, and sensor 14. The circuit board 26, the controller 28, the transmitter 30, and the battery 32 may be contained in a sealed compartment 34 such that they are configured to not directly contact the subject 2 when implanted. The sealed compartment 34 may be advantageous to separate these components from the other parts of the implantable device 12, as these components may not be rated for direct in vivo bodily contact, in contrast with the implant 16, which is constructed from biocompatible materials. An ultrasound couplant may be disposed between the transmitter 30 and the sealed compartment 34, or the sealed compartment 34 and the implant 16, such that the device 12 has a single resonance frequency.

The transmitter 30 may be configured to transmit sensed data from the sensor 14 wirelessly and transcutaneously by short-wavelength ultra high frequency radio waves in the medical radio band from about 2.4 to 2.485 GHz (i.e., BLUETOOTH®).

The transmitter may be configured to have a power consumption of between 0.5 mW and 80 mW, 1 mW and 60 mW, and 2.0 mW and 40 mW, 10 mW, 5 mW, or any subrange thereof. The transmitter 30 may consume about 20 mW of power when in operation. The transmitter 30 may be configured to transmit data at least four inches through water at a rate of 5 values per second (1 kb/s) with a data reliability of 95%. Data reliability transmitted from the transmitter at these power levels may be at least 95%, at least 98%, at least 99%, at least 99.9%, or 100%. "Data reliability" means reliability over 10 minutes as calculated from a bit error rate (BER).

Transmitter power may be less than 20 mW, such as less than 5 mW. Signal to noise may be less than 30 dB, such as 10 dB. In embodiments of the system 10 having the piezoelectric transducer transmitter 30, a piezo phase array (PPA) which may utilized to focus the vibration into a specific location (for example, the implant).

Advantageously, the wireless transcutaneous sensor 14 enables data, such as force, to be measured from the sensor 14 in vivo when the sensor 14 is implanted with an implant 16. This benefit is especially advantageous in embodiments where the implant is adjustable in vivo, such as the case in magnetically adjustable implant systems, such as MAGEC® magnetically adjustable implant systems for spinal and limb lengthening procedures sold by NuVasive, Inc. of San Diego, Calif. Such adjustable systems are disclosed in, for example, U.S. Pat. Nos. 9,398,925 and 9,393,117, which are incorporated by reference herein in their entireties.

The system 10, including its various components, may be provided in a kit for use (i.e., implantation) during spinal correction and limb lengthening surgical procedures.

Figure 3:
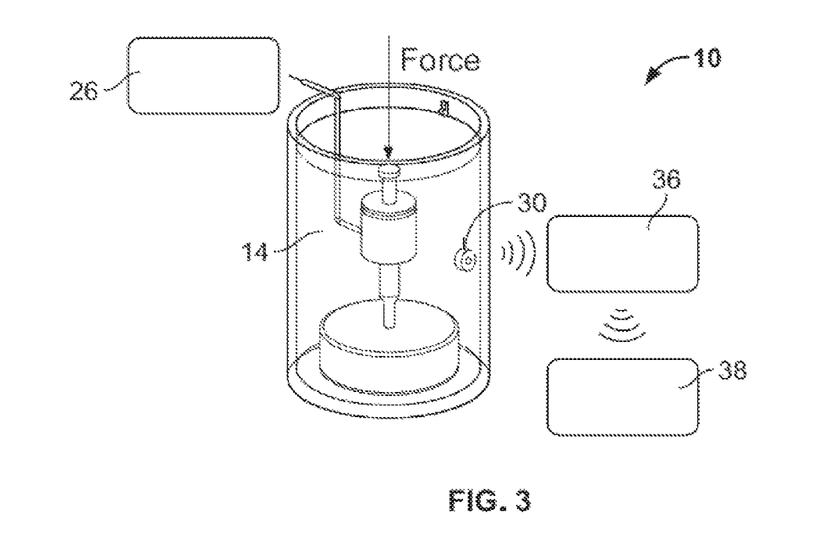
FIG. 3 shows a partial view of yet another embodiment a sensor system.

As shown in FIG. 3, the system 10 may wirelessly transmit data sensed by the subcutaneous sensor 14 from the transmitter 30 to a receiver 36 external to the subject 2. Receiver output may be less than 1 mV, such as 0.2 mV. The receiver 36 may be wearable by the subject 2 (e.g., coupled with an article of clothing or accessory to be worn by the subject 2) or may be a computer system external and proximate to the subject 2. This data transmission from the transmitter 30 to the receiver 36 may be carried by ultrasound sound waves. The receiver 36 may receive the data transmission from the transmitter 30, and process the data to transmit the sensed data to a mobile device 38 by short-wavelength ultra high frequency radio waves in the medical radio band from about 2.4 to 2.485 GHz.

Figure 4:
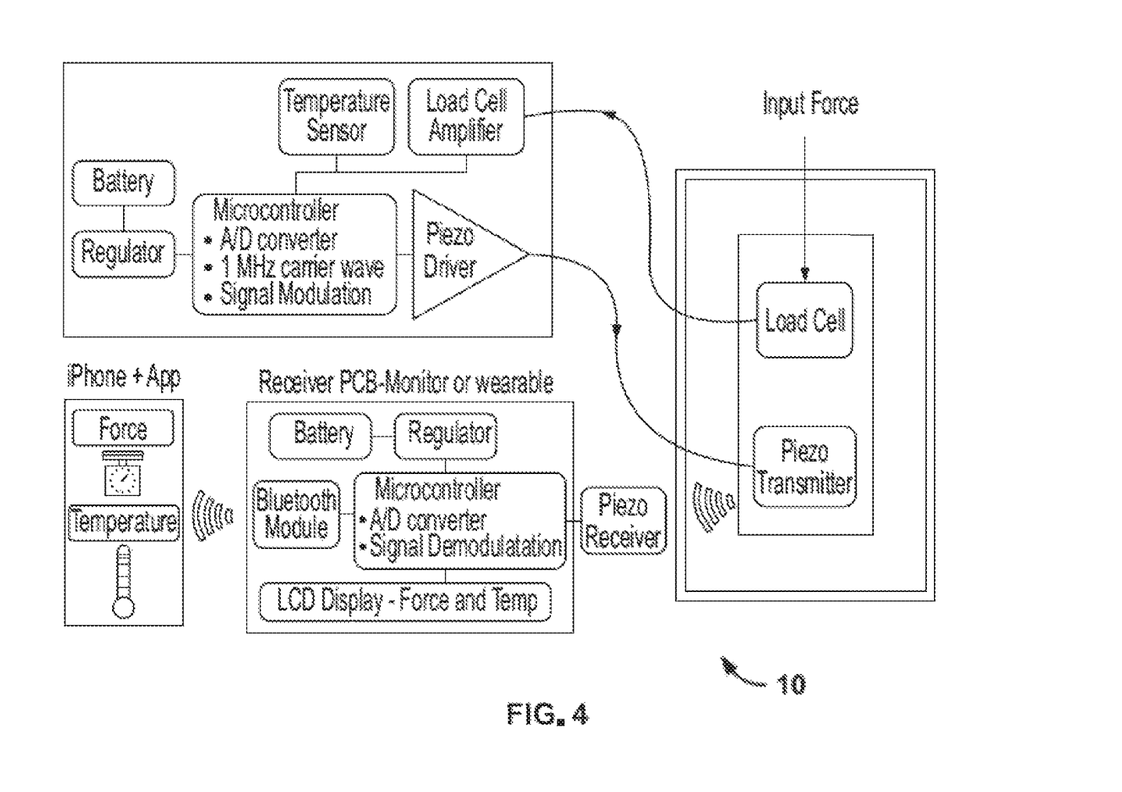
FIG. 4 shows a flowchart of an embodiment of a sensor system.

This dual-wireless capability is advantageous, as, for example, ultrasound sound waves are effective when employed at short distances and transcutaneously (such as when receiver 36 is worn on the body of the subject 2), and it enables the system 10 to be interoperable with many existing mobile devices 38, such as smartphones, laptops, external remote controls, cloud computer systems, or tablets, which are configured to receive ultra high frequency radio waves in the medical radio band from about 2.4 to 2.485 GHz. FIG. 4 illustrates a flow chart of an embodiment of the system 10, particularly how components of an embodiment of the system 10 communicate data and/or power with each other. Wires that connect these components of the system may be shielded, such as by epoxy.

Figure 5:
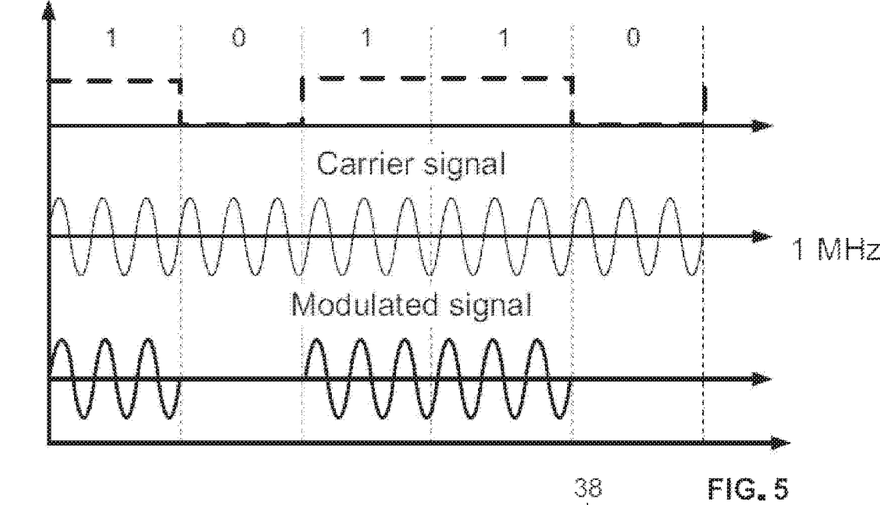
FIG. 5 shows techniques of modulations with a carrier signal in accordance with an embodiment of a sensor system.

As shown in FIG. 5, wireless signals carrying the sensed data may be modulated for wireless transmission. Suitable forms of modulation include on-off keying, amplitude shift keying (ASK), frequency shift keying (FSK), phase shift keying (PSK), and analogue frequency modulation. Advantageously, signals that are modulated may require less power than non-modulated signals and may be received farther away from the transmitter 30 than non-modulated signals. Modulated signals may also have a greater accuracy than non-modulated signals.

Figure 6A:
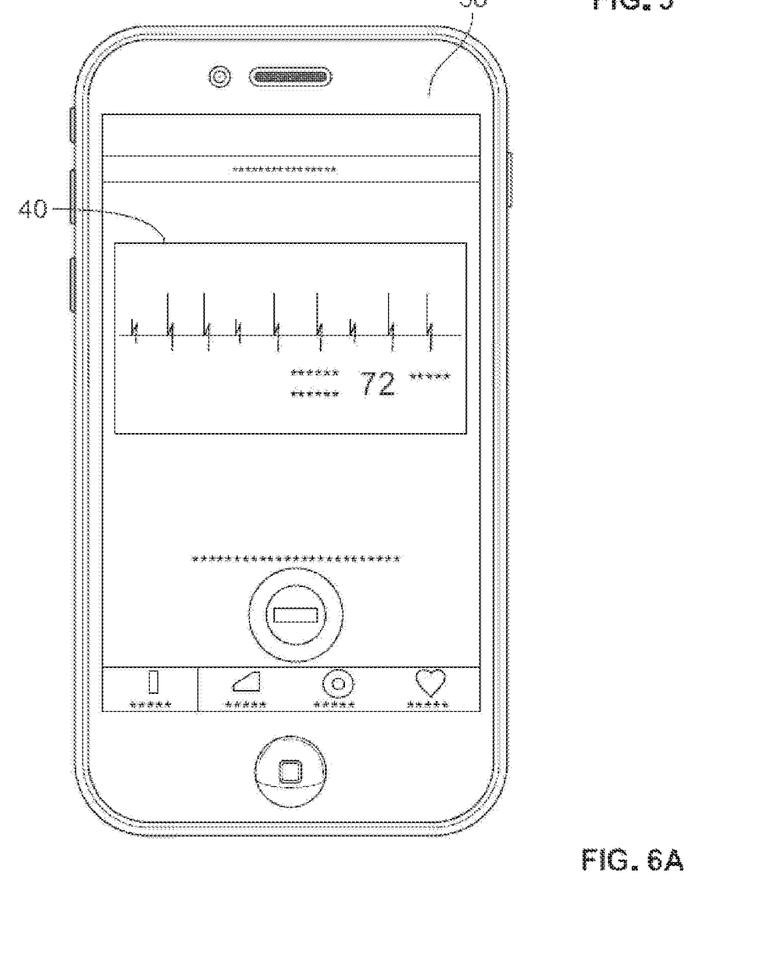
FIGS. 6A-6C illustrate graphical user interfaces on a mobile device in accordance with an embodiment of a sensor system.
Figure 6B:
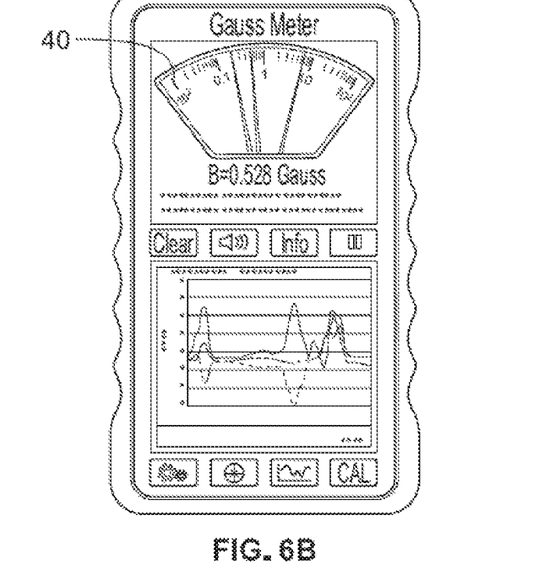
Figure 6C:
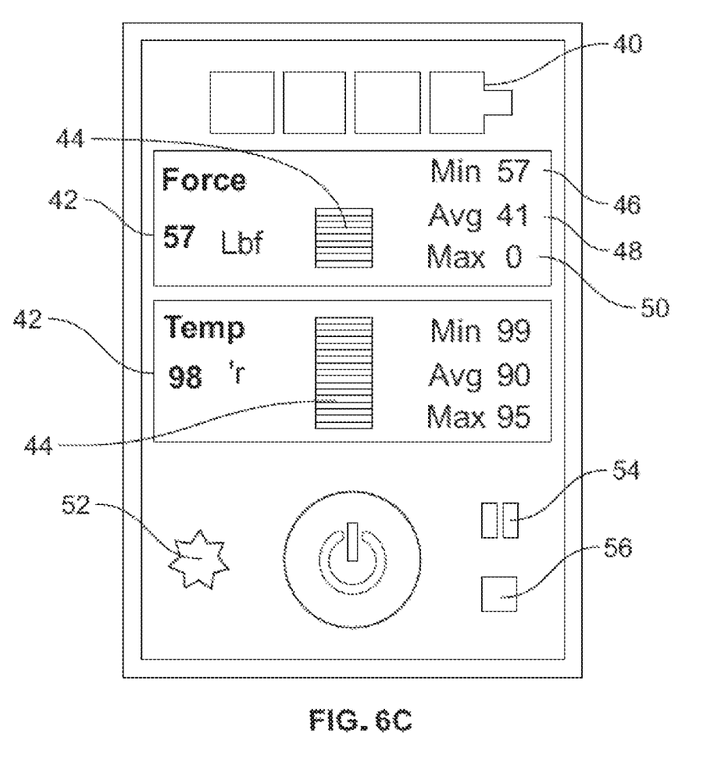

FIGS. 6A-6C illustrate screenshots of the mobile device 38 containing computer executable instructions configured to receive, process, and display the sensed data from the subcutaneous sensor 14. The mobile device 38 may contain a graphical user interface (GUI) 40 that displays sensed data to users, such as patients and physicians, and allows users to control the system 10 via the computer executable instructions. As shown in FIG. 6C, the GUI 40 may display sensed data 42 (force and temperature, as shown), and provide a graphical representation 44 of the sensed data. The GUI 40 may display, and the system 10 store, the maximum value 46, the average value 48, and the minimum value 50 of the sensed data. The GUI 40 may also be configured to allow a user to control settings 52 of the system 10, pause/start 54 the system 10, reset 56 the system 10, and power on and off 58 the system 10.

FIGS. 7A-8D illustrate screenshots of a mobile device having computer readable instructions configured to communicate with the subcutaneous sensor 14 according to another embodiment of the system 10. The computer executable instructions stored on the mobile device 38 may be configured to record 60 sensed data over time for later viewing, such as by a physician. The computer executable instructions may indicate whether the mobile device 38 is actively communicating (i.e., connected) with the sensor 14. The computer readable instructions may be configured to display sensed data on the mobile device 38 in metric and/or English (i.e., imperial) units.

Figure 7A:
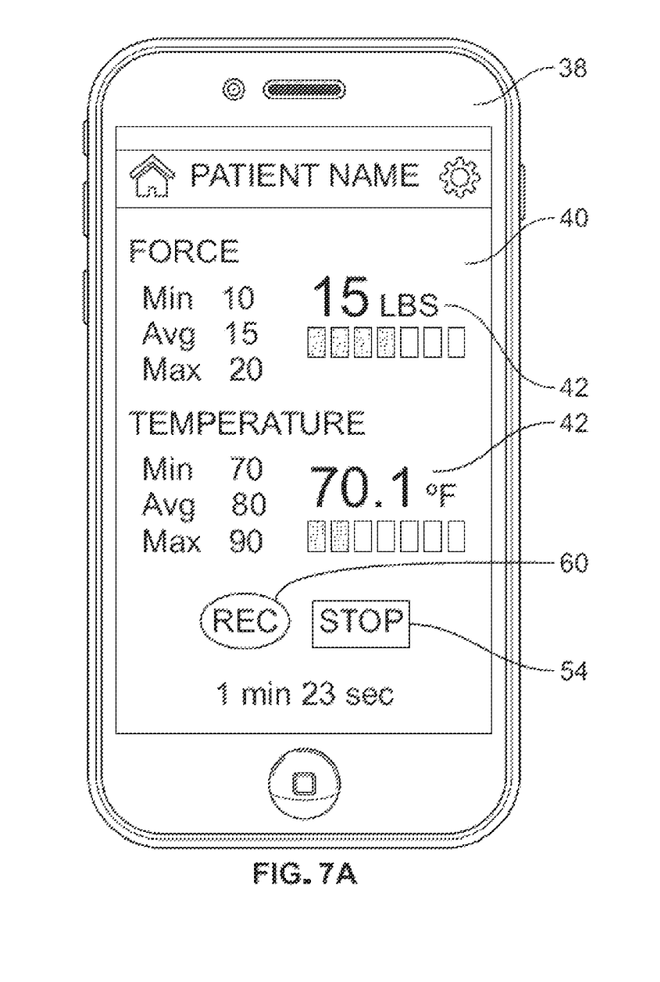
FIGS. 7A-7C illustrate graphical user interfaces on a mobile device in accordance with an embodiment of a sensor system.
Figure 7B:
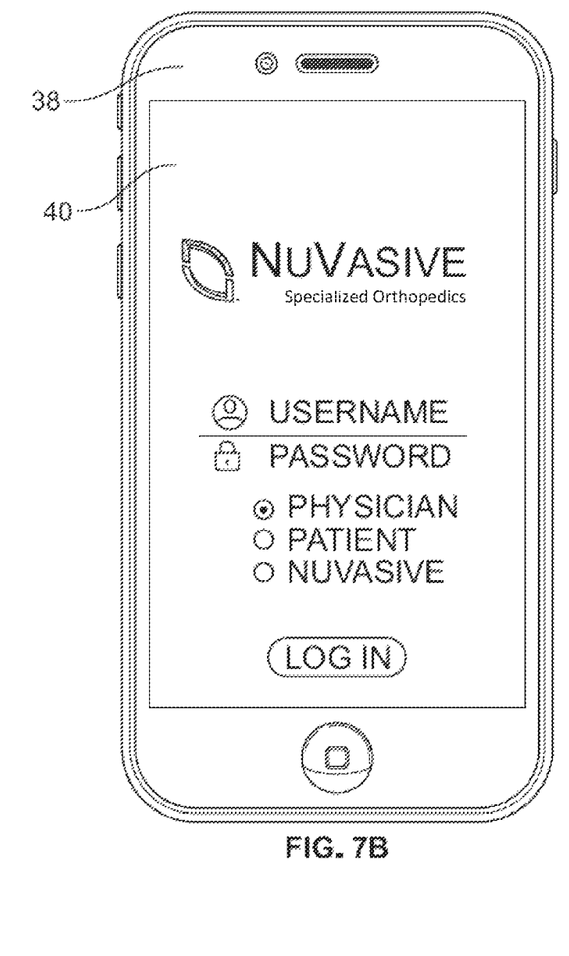
Figure 7C:
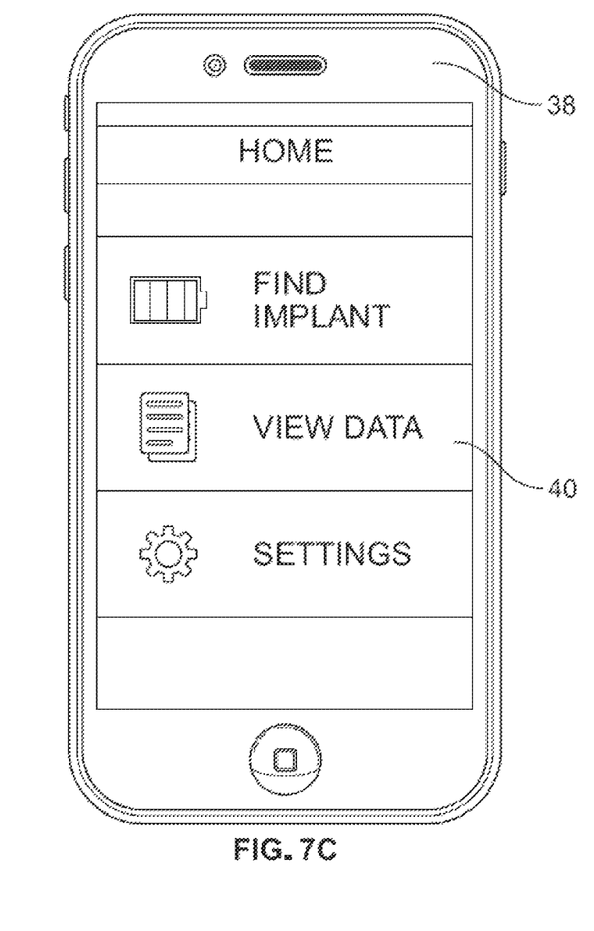
Figure 8A:
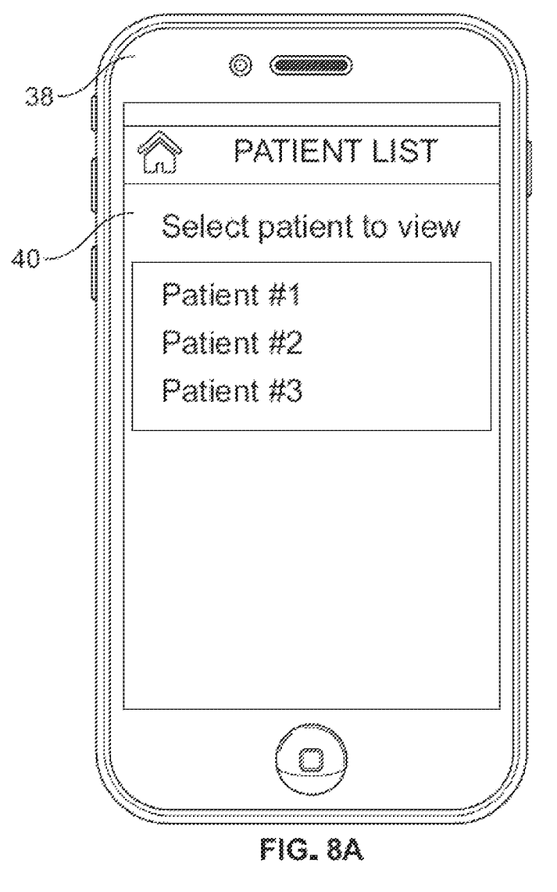
FIGS. 8A-8D illustrate graphical user interfaces on a mobile device in accordance with an embodiment of a sensor system.
Figure 8B:
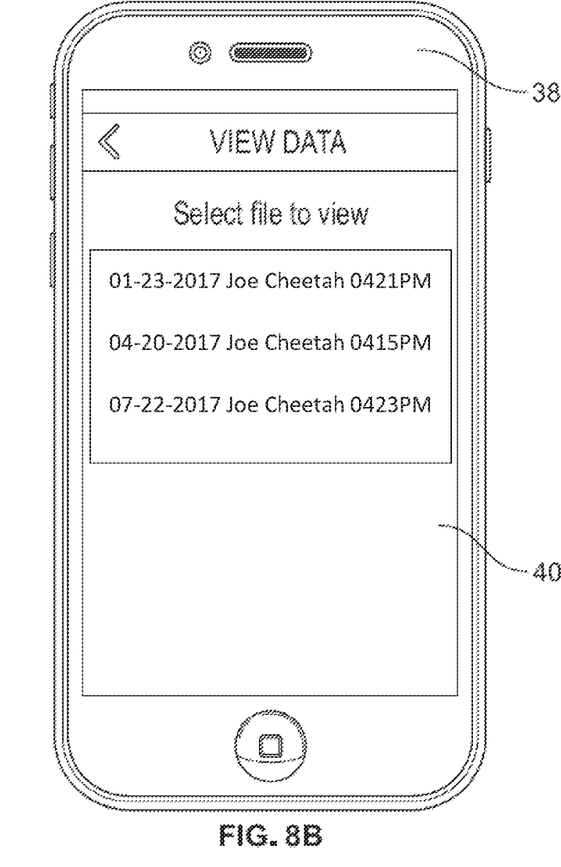

As shown in FIG. 7B, the computer program may contain computer executable instructions configured to selectively limit functions or data to different types of users, such as between physicians, patients, and device service providers. By way of example, physicians may be able to access data from multiple patients (as shown in FIG. 8A), while the computer executable instructions are configured to restrict access to patient data by security measures, such as a password, to other types of users. Similarly, the computer executable instructions are configured to restrict access to features that data that is desired to only be provided to device service providers by security measures, such as passwords. As illustrated in FIG. 8B, the computer executable instructions may be configured to store and allow users to individually access sensed data from different sessions in time.

Figure 8C:
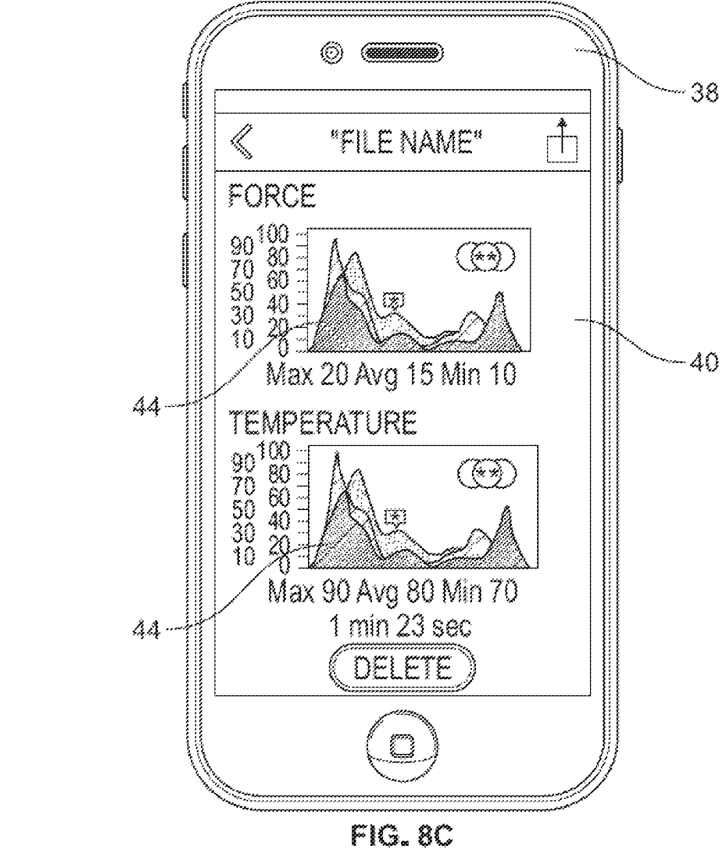
Figure 8D:
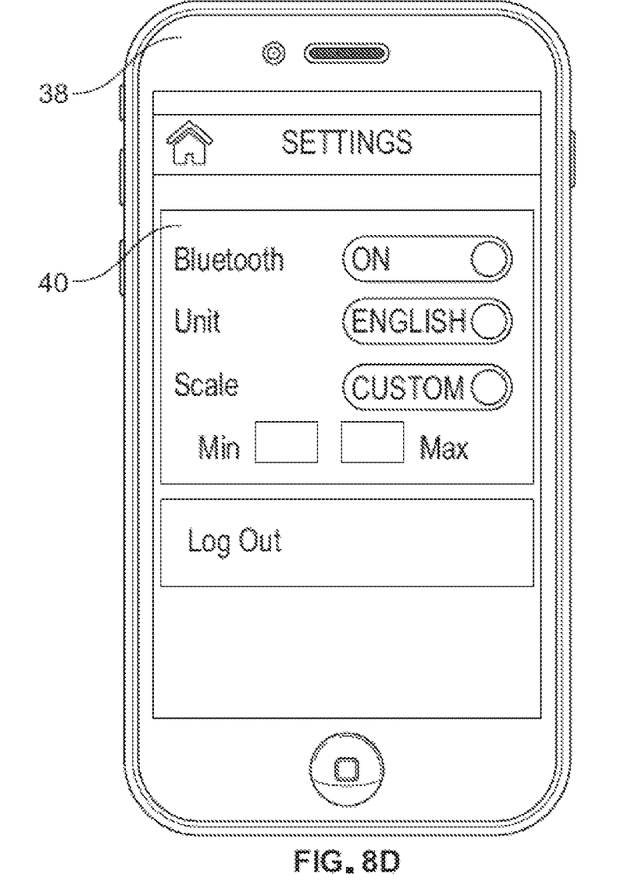

As shown in FIG. 8C, the computer executable instructions may be configured to include a sharing feature 62 such that users of the mobile device 38 may be able to share sensed data by, for example, e-mail, text message, and social media, directly through the computer executable instructions of the mobile device 38. Further, as shown in FIG. 8D, the computer executable instructions may enable users to customize BLUETOOTH® functionality (on/off) of the mobile device 38, select between English or metric units, and control the scale of the GUI 40 on the mobile device 38, including auto-scale and a custom scale.

Figure 9:
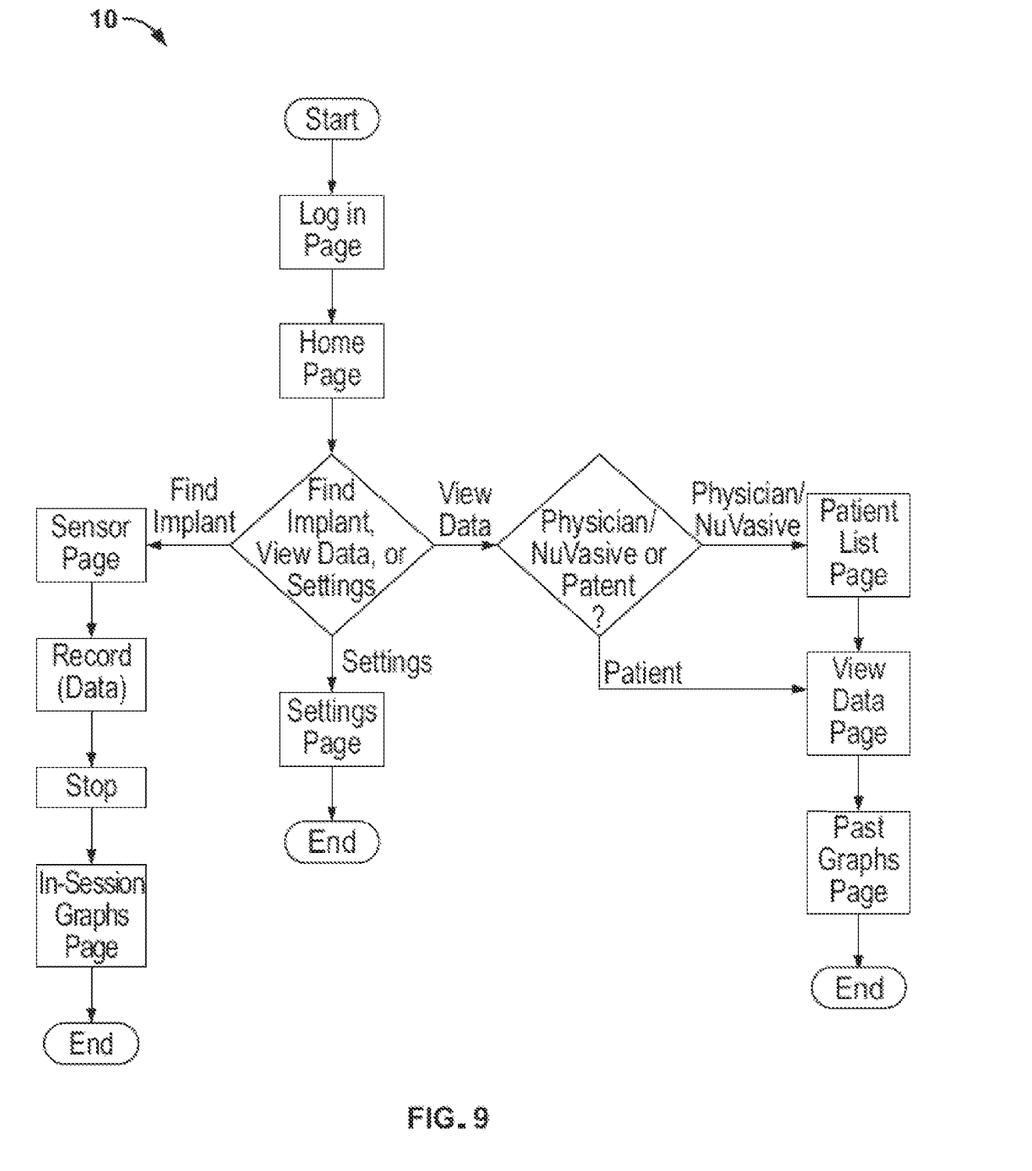
FIG. 9 illustrates a flow chart of the computer executable instructions stored on a mobile device in an embodiment of a sensor system.

FIG. 9 shows a flowchart of the computer readable instructions according to an embodiment of the system 10.

The present disclosure also provides a method of transcutaneously transmitting data from the subcutaneous sensor 14 positioned within the subject 2 and/or a method of measuring data at an implant site of the subject 2. A method is also disclosed to determine strain in rods to predict failure, and to determine health and progress of fusion. A method is provided to measure an applied force using the system 10 of the present disclosure in order to control growth of bones by utilizing the Heuter Volkman principle (i.e., that bones grow faster when placed under a tensile load). Thus, the system 10 can be utilized to maintain an ideal compressive load on desired bones, which can be used to control bone growth in facial surgery, long bones, extremities (fingers, toes, etc.), and apex correction for scoliosis). The system 10 may be used in a method of distraction osteogenesis, monitor bone quality of fusion, and detect stroke or movement of the device 12. The system 10 may be used in connection with pharmacological agents such that if the sensors 14 that detect slower rates of bone growth or fusion below a predetermined level, a growth promoting pharmacological agent (e.g., bisphosphonates) is stored at the implant site and released locally to promote bone formation. Similarly, the sensors 14 detect inflammation or a rise in temperature, the sensors 14 could instruct the implant 16 to release a pharmacological agent locally to reduce the cause, such as an infection.

A method is disclosed herein that includes measuring force in the implant 16 to determine, and monitor, patient compliant with a treatment plan (i.e., recommended levels of activities after surgery). By recording force over time, one can determine if the patent 2 is compliant with recommended activities.

A method is disclosed herein where the implant 16 is automatically adjusted (i.e., to increase force) if the system 10 senses that compression across a facture site is not above a predetermined level.

A method is disclosed herein to measure force in an instrument when distracting or compressing pedicle screws across a graft in a spine of the subject 2.

A method is disclosed herein to measure force and automatically adjust tension in sutures or tethering devices. If the force sensor 14 determines a predetermined tension has been met, the system 10 transmits instructions to the implant 16 to tighten to tension, or alerts the physician that the tension should be modified.

A method is described herein where the system monitors intradiscal pressure to help subjects 2 to understand how to have less pressure on their discs during activities. The sensor 14 is disposed between discs of the subject 2.

The methods described herein include transcutaneously transmitting wireless power (including indirectly) to the subcutaneous sensor 14, sensing data with the subcutaneous sensor 14, and transcutaneously transmitting sensed data (including indirectly) from the subcutaneous sensor 14. The sensed data may be received by a subcutaneous or external receiver 36. The data may be transmitted to the receiver 36 by ultrasound sound waves, which may be modulated. The receiver 36 may be configured to transmit data, including transcutaneously if internal, to the mobile device 38, such as by BLUETOOTH®.

Working Example 1

Figure 10:
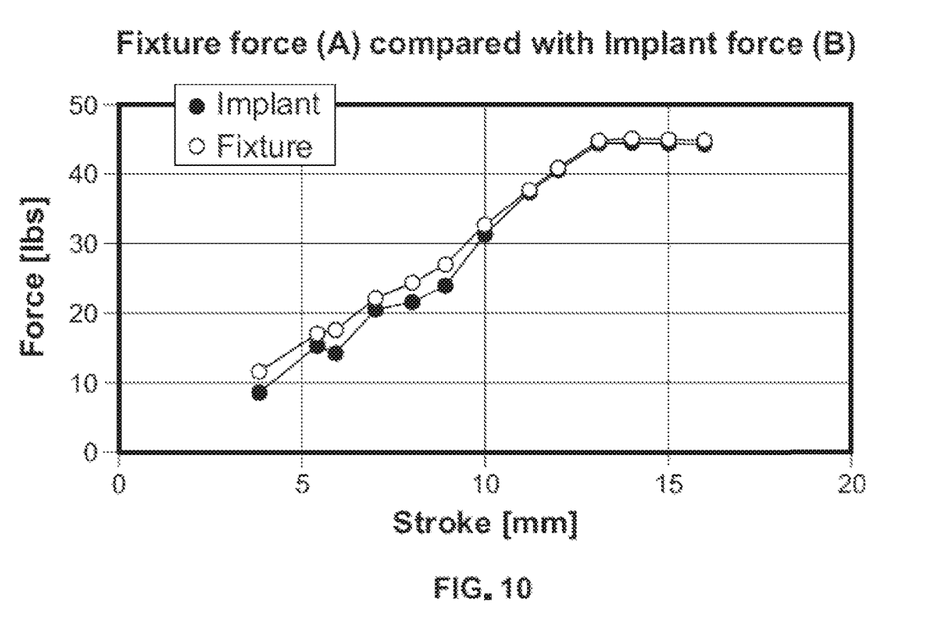
FIG. 10 illustrates a graphical view of force exerted on a fixture compared with forced measured on an implant in an embodiment of a sensor system.

The sensor 14 in accordance with the present disclosure was placed within a fixture, a predetermined force was exerted on the fixture, and the sensor measured the force exerted on the fixtures. FIG. 10 illustrates a graph comparing the predetermined force (fixture force) with the sensed force (implant force). As can be seen, the sensed force matches the fixture force+/− within 3 pounds. The difference between the fixture force and the sensor force can be explained by, for example, internal friction of the fixture.

Working Example 2

A tubular piezoelectric transducer was placed within a housing of a metal adjustable length spinal rod (i.e. tubular). A gap between the piezoelectric transducer and housing metal was filled with an ultrasound couplant. The ultrasound couplant matches the acoustic impedance between two different materials.

The piezoelectric transducer's ability to send RF-like signal was tested and verified. The adjustable length spinal rod housing containing the tubular piezoelectric transducer ("Implant PT") was placed inside of a water bath in the jug, then another piezoelectric transducer was placed on the wall of the jug (the "Reader PT").

Figure 11A:
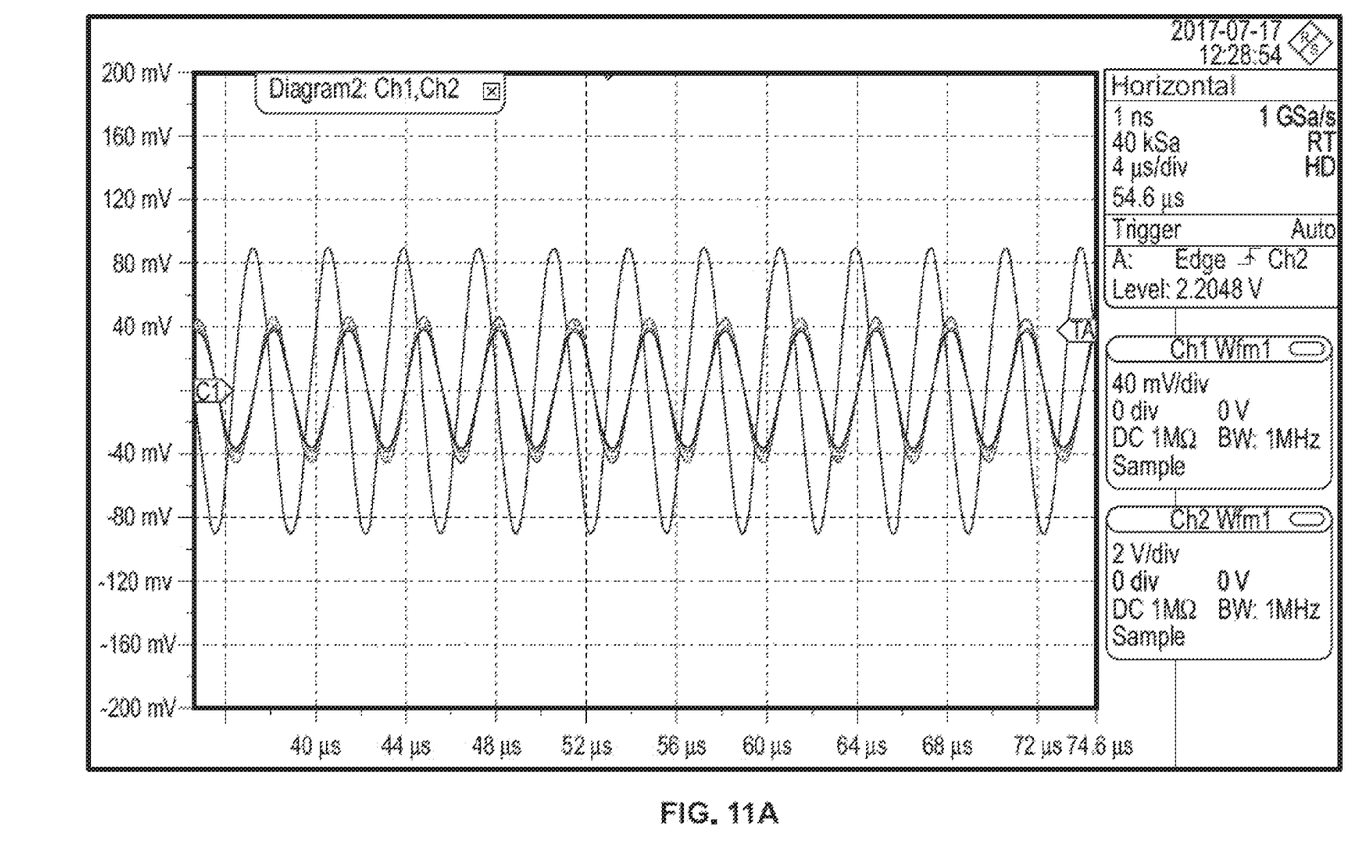
FIG. 11A illustrates an applied sinusoidal voltage to an implant and the detected vibration according to an embodiment of a sensor system.

As shown in FIG. 11A, the implant piezoelectric transducer was excited (applied with a sinusoidal voltage) and the piezoelectric transducer created a vibration, which traveled through the couplant, through the metal housing tube, through the water, through the plastic jug, and it was finally detected by the Reader PT.

Figure 11B:
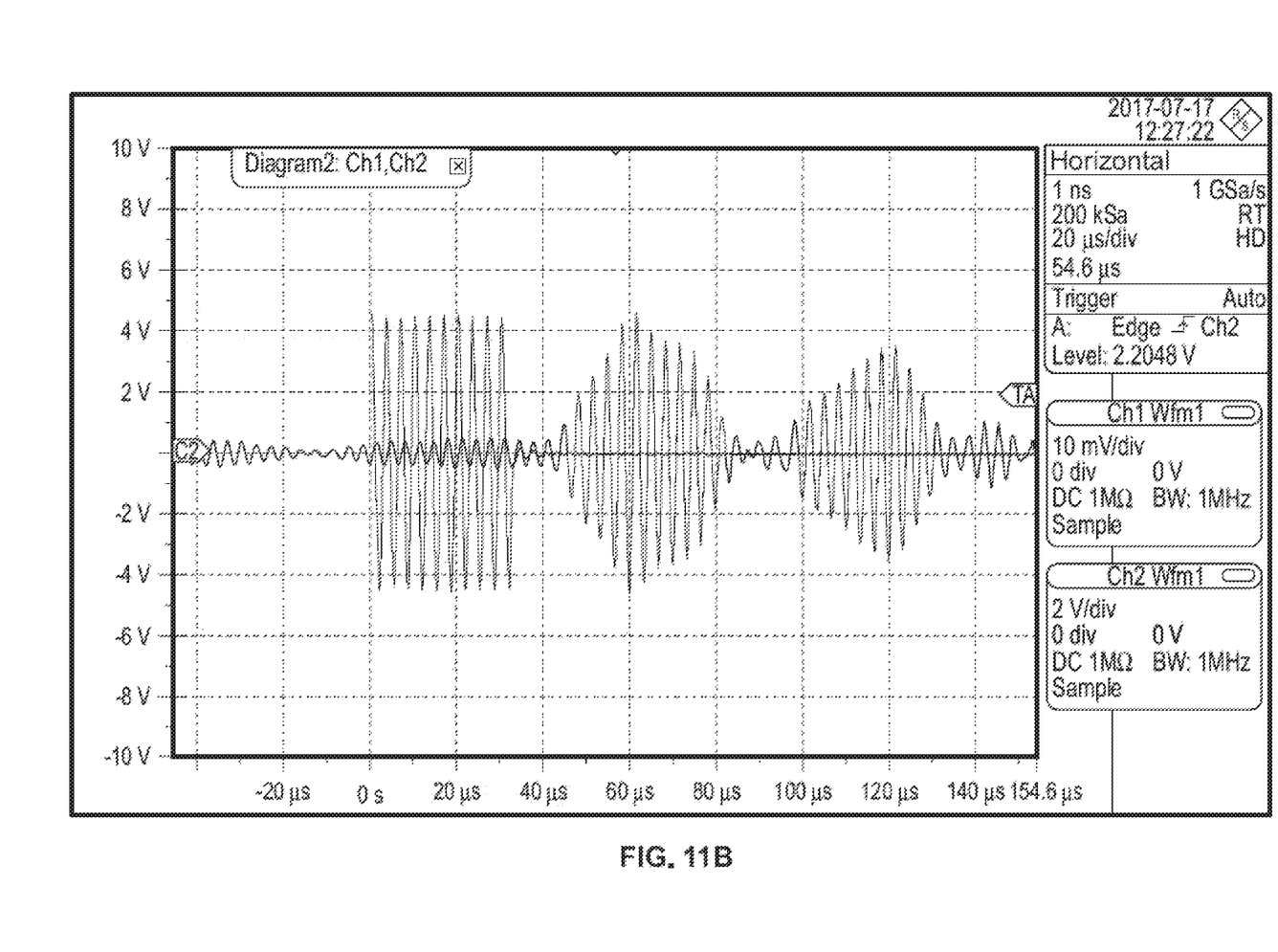
FIG. 11B illustrates an acoustic energy transfer between two piezoelectric transducers, wherein one transducer is exciting the other transducer in accordance with an embodiment of a sensor system. The response is delayed because of the distance created between the two transducers.

The data signal may be modulated, which advantageously, significantly reduces the size of the energy storage device needed. See, for example, FIG. 11B. Electrical signal was applied to the reader piezoelectric transducer 30, which is converted into vibration. According to some embodiments, using, for example, a MAGEC® rod, the frequency used was the structural resonant frequency of the implant magnet, which forces the vibration to remain even after the driving force is removed. When the driving signal stopped after a few square waves, which is enough to drive the implant piezoelectric transducer 30 to resonate, the implant signal was tailing down. The tail end of this signal can be modulated to, and sent back to, the reader piezoelectric transducer 30.

I claim:

1. An implantable device for sensing data comprising:
a subcutaneous sensor configured to couple with an implant, the subcutaneous sensor configured to sense data and transmit the sensed data to a circuit board;
wherein the implant includes:
the circuit board configured to receive data sensed by the subcutaneous sensor and communicate the sensed data to a controller;
the controller configured to transmit the sensed data to a transmitter; and
the transmitter configured to wirelessly and transcutaneously transmit data sensed by the subcutaneous sensor using an ultrasound data signal,
wherein the transmitter includes a tubular piezoelectric transducer, the tubular piezoelectric transducer extends longitudinally along a longitudinal axis of the implant, and the tubular piezoelectric transducer is configured to propagate data radially covering 360 degrees to a receiver external to a subject into which the implantable device is positioned.

2. The device of claim 1, wherein the device is configured to operably receive energy from ultrasound sound waves and provide energy to the subcutaneous sensor.

3. The device of claim 2, wherein the ultrasound sound waves have a frequency of greater than about 20 kilohertz.

4. The device of claim 1, wherein the piezoelectric transducer is in communication with the subcutaneous sensor.

5. The device of claim 1, wherein the tubular piezoelectric transducer is configured to subcutaneously receive energy by ultrasound sound waves and wirelessly and subcutaneously transmit data sensed by the subcutaneous sensor by ultrasound sound waves.

6. The device of claim 1, wherein the implant is selected from the group consisting of: a spinal rod, an intramedullary rod, and a spinous process spacer.

7. The device of claim 1, wherein the wirelessly transmitted sensed data is transmitted by short-wavelength ultra high frequency radio waves in the medical radio band from about 2.4 to 2.485 GHz.

8. A method of transcutaneously transmitting data from a subcutaneous sensor positioned within a subject, the subcutaneous sensor configured to couple with an implant, wherein the implant includes a circuit board, and wherein the subcutaneous sensor configured to sense data and transmit the sensed data to the circuit board, the circuit board configured to receive data sensed by the subcutaneous sensor and communicate the sensed data to a controller, and the controller configured to wirelessly and transcutaneously transmit data sensed by the subcutaneous sensor using an ultrasound data signal, the transmitter includes a tubular piezoelectric transducer,
wherein the tubular piezoelectric transducer extends longitudinally along a longitudinal axis of the implant, and the tubular piezoelectric transducer is configured to propagate data radially to a receiver external to a subject into which the implantable device is positioned;
the method comprising:

transcutaneously transmitting wireless power to a receiver external or subcutaneous to the subject;
sensing data with the subcutaneous sensor; and
transcutaneously radially transmitting sensed data from the subcutaneous sensor covering 360 degrees.

9. The method of claim 8, wherein the sensed data is force data, temperature data, electrical data, pH data, distance data, pressure data, biomolecular data, or a combination thereof.

10. The method of claim 8, wherein the transmitting wireless power comprises transmitting power wirelessly by ultrasound sound waves, and wherein the transmitting sensed data comprises transmitting by ultrasound sound waves.

11. The method of claim 8, further comprising receiving sensed data with a subcutaneous controller.

12. The method of claim 11, wherein the subcutaneous receiver is configured to subcutaneously transmit data to a mobile device, and
wherein the transmitted sensed data is transmitted to the mobile device by short-wavelength ultra high frequency radio waves in the medical radio band from about 2.4 to 2.485 GHz.

13. The method of claim 8, further comprising amplitude modulating the sensed data during the wireless transmission.

14. An implant kit, comprising:
an implant configured to be implanted in a subject; and
a subcutaneous force sensor configured to couple with the implant, the subcutaneous force sensor configured to sense force data associated with an applied force of the implant and transmit the sensed data to a circuit board;
wherein the implant includes:
the circuit board configured to receive data sensed by the subcutaneous sensor and communicate the sensed data to a controller;
the controller configured to transmit the sensed data to a transmitter;
a force-load coupler configured to interface between the implant and the subcutaneous force sensor; and
the transmitter configured to wirelessly receive power and configured to wirelessly and transcutaneously transmit the force data sensed by the subcutaneous force sensor via an ultrasound data signal, wherein the transmitter includes a tubular piezoelectric transducer, the tubular piezoelectric transducer extends longitudinally along a longitudinal axis of the implant, and the tubular piezoelectric transducer is configured to propagate data radially covering 360 degrees to a receiver external to a subject into which the implantable device is positioned.

15. The implant kit of claim 14, wherein the wireless power is transmitted by ultrasound sound waves.

16. The implant kit of claim 14, wherein the transmitter is a piezoelectric transducer configured to subcutaneously and wirelessly receive power and transmit power to the subcutaneous force sensor.

17. The implant kit of claim 14, wherein the controller is configured to perform at least one of: processing of the force data and storing of the force data.

18. The implant kit of claim 14, wherein the controller communicates the force data to the transmitter.

19. The device of claim 1, further comprising:
a force-load coupler configured to interface between the implant and the subcutaneous sensor.

20. The device of claim 1, wherein the circuit board is configured to communicate data sensed by the subcutaneous sensor to a controller for at least one of processing and storage, wherein the controller is configured to transmit data sensed by the subcutaneous sensor to the transmitter.

* * * * *